United States Patent [19]

Canova-Davis et al.

[11] Patent Number: 4,783,400
[45] Date of Patent: * Nov. 8, 1988

[54] HOMOGENEOUS ENZYME IMMUNOASSAY SYSTEM AND METHOD

[75] Inventors: Eleanor Canova-Davis, South San Francisco; Viola T. Kung, Menlo Park; Carl T. Redemann, Walnut Creek, all of Calif.

[73] Assignee: Cooper Lipotech, Menlo Park, Calif.

[*] Notice: The portion of the term of this patent subsequent to Nov. 11, 2003 has been disclaimed.

[21] Appl. No.: 898,440

[22] Filed: Aug. 20, 1986

Related U.S. Application Data

[63] Continuation-in-part of Ser. No. 699,860, Feb. 8, 1985, Pat. No. 4,622,294.

[30] Foreign Application Priority Data

Feb. 7, 1986 [CA] Canada ................................. 501398
Feb. 7, 1986 [WO] PCT Int'l Appl. ... PCT/US86/00279

[51] Int. Cl.$^4$ ............................................. G01N 33/53
[52] U.S. Cl. ............................................. 435/7; 435/14;
  435/26; 435/177; 435/188; 435/810; 436/528;
  436/535; 436/815; 436/816; 436/821; 436/829
[58] Field of Search .................. 435/7, 14, 26, 177,
  435/188, 810; 436/528, 535, 815, 816, 821, 829

[56] References Cited

U.S. PATENT DOCUMENTS

| 4,322,311 | 3/1982 | Lim et al. ................. | 424/85 |
| 4,338,094 | 7/1982 | Elahi ......................... | 435/7 |
| 4,342,826 | 8/1982 | Cole .......................... | 435/7 |
| 4,473,638 | 9/1984 | Auditore-Hargreaves | 435/7 |
| 4,532,089 | 7/1985 | MacDonald ............. | 436/829 |
| 4,581,222 | 4/1986 | Baldeschwieler et al. | 424/1.1 |
| 4,622,294 | 11/1986 | Kung et al. .............. | 435/7 |

FOREIGN PATENT DOCUMENTS

| 135129 | 3/1985 | European Pat. Off. ............... | 435/7 |
| 140521 | 5/1985 | European Pat. Off. ............... | 435/7 |
| 84/02579 | 7/1984 | World Int. Prop. O. ............. | 435/7 |

*Primary Examiner*—Christine M. Nucker
*Attorney, Agent, or Firm*—Ciotti & Murashige, Irell & Manella

[57] ABSTRACT

A liposome assay reagent for determination of an analyte in a homogeneous immunoassay. The reagent includes a suspension of oligolamellar lipid vesicles containing encapsulated glucose-6-phosphate dehydrogenase (G6PD), at a specific activity of between about 1–15 units/$\mu$mole vesicle lipid, and glucose-6-phosphate (G6P) at a concentration of at least about 5 mM. The encapsulated G6P protects the enzyme against inactivation on preparation, by reverse phase evaporation in the presence of organic solvent, and on storage as an aqueous suspension.

6 Claims, 2 Drawing Sheets

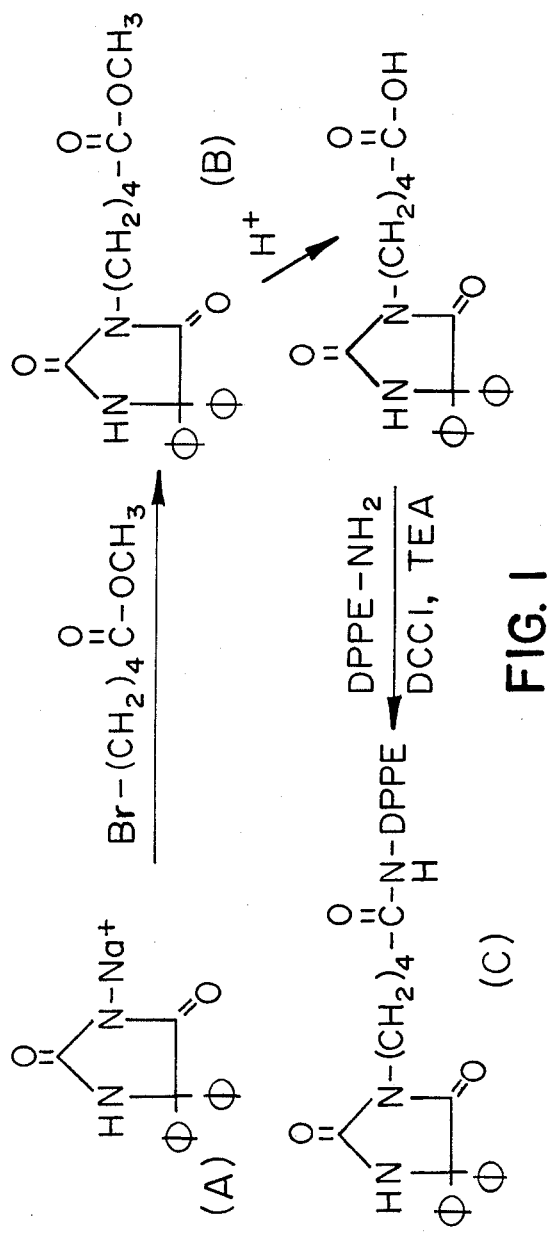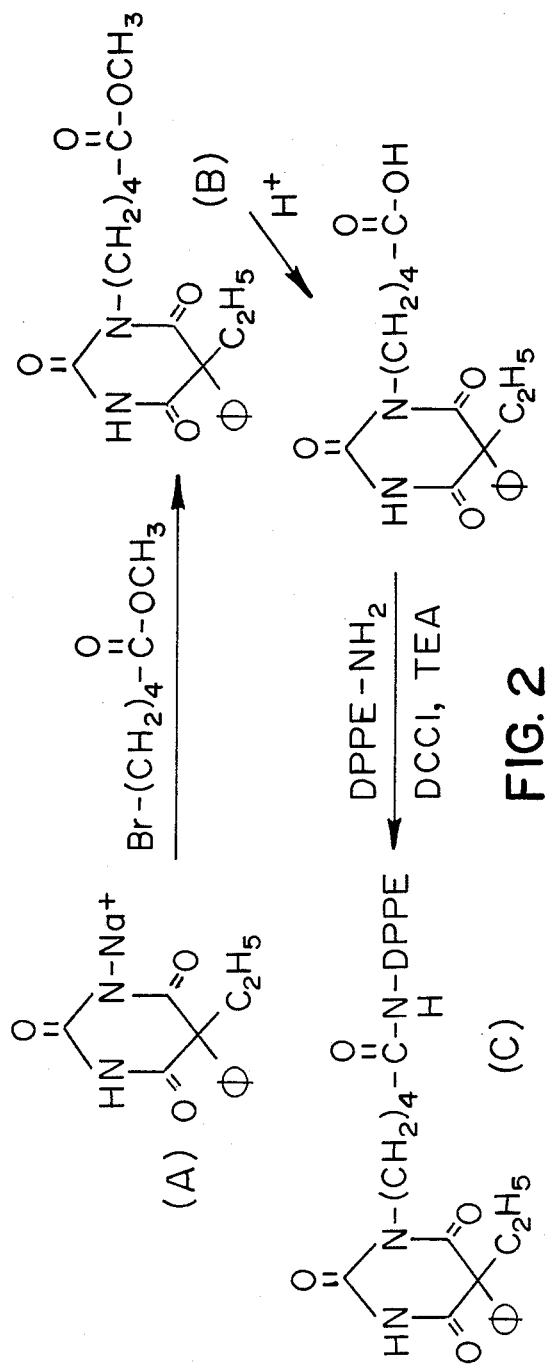
FIG. 1
FIG. 2

HOMOGENEOUS ENZYME IMMUNOASSAY SYSTEM AND METHOD

CROSS-REFERENCE TO RELATED APPLICATION

This is a continuation-in-part of U.S. patent application Ser. No. 699,860, filed Feb. 8, 1985, now U.S. Pat. No. 4,622,294.

FIELD OF THE INVENTION

The present invention relates to liposome immunoassays, and to a reagent for use in determination of an analyte in a homogeneous liposome immunoassay.

References

The following references are referred to herein by correspondig number:

1. Yasuda, T., et al, *J Immunol Methods* (1981) 44:153.
2. Geiger, B., et al, *J Immunol Methods* (1977) 17:7.
3. Uemura, K., et al, *J Immunol Methods* (1982) 53:221.
4. Deamer, D., et al, *Biochim Biophys Acta* (1976) 443:629.
5. Cafiso, D. S. et al, *Biochim Biophys Acta* (1981) 649:229.
6. Schieren, H., et al. *Biochem Biophys Acta* (1978) 542:137.
7. Szoka, F., et al *Proc Natl Acad Sci (USA)* (1978) 75:4194.
8. Szoka, F., et al, *Ann Rev Biophys Bioeng* (1980) 9:467.
9. Kirby, C. J., et al, *Liposome Technology*, Gregoriadis, G., et., Vol. 1, CRC Press Inc., Boca Raton, Florida.
10. Muller-Eberhard, H. J., et al, *Ann Rev Biochem* (1975) 44:697.
11. Stroud, R. M. et al, *Immunochemistry of Proteins*, (1979) Atazzi, M. Z. ed, Vol 3, Plenum Press, NY, NY 3.
12. Whicher, J. T., *Clin Chem* (1978) 24:7.
13. Huang, A., et al, *J Biol Chem* (1980) 255:8015.
14. Heath, T. D. et al, *Biochem Biophys Acta* (1981) 640:66.
15. Martin F. J.. et al. *Biochemistry* (1981) 20:4229.
16. Martin F. J.. et al. *J Biol Chem* (1982) 257:286.
17. Cook, C. E., et al, *Path Pharm* (1976) 13:497.
18. Cook. C. E., et al *Chem Path Pharm* (1973) 5:767.

BACKGROUND

The ability of complement to recognize ligand/antiligand binding events on the surface of lipid vesicles, leading to complement-mediated vesicle lysis, has been exploited in immunoassays. Yasuda, et al have described a simple method for measuring anti-glycolipid antibody by reacting the antibody with complement and liposomes containing surface glycolipid, where complement-mediated cell lysis and release of a fluorogenic reporter from the liposomes produces increased fluorescence in the assay medium (reference 1). Similar types of liposome immunoassays applicable to ganglioside $GM_2$ antigen (reference 2), and to Forsmann, and blood group A-reactive gangliolipids (reference 3) have been reported.

Immunoassay systems involving lysable lipid membrane vesicles provide important potential advantages in diagnostic test systems. One advantage is that the ligand/anti-ligand binding reaction and the measurement of released reporter from lysed cells, can be performed in the same assay mixture. This single-mixture assay, which is referred to as a homogeneous assay, contrasts with "solid-phase" enzyme or fluorescent immunoassays which involve the steps of (1) binding a ligand-reporter complex to a solid surface in the presence of analyte in one mixture, (2) separating the solid and liquid phases, and (3) measuring bound or unbound reporter levels in the solid or liquid phases, respectively. Homogeneous cell-lysis immunoassays also have the potential for high assay sensitivity, since relatively few ligand/anti-ligand binding events on the vesicle surface can lead to the release or expression of a large number of reporter molecules.

Several types of encapsulated reporter compounds have been used in lipid-vesicle reagents in immunoassays of this type. Chromogenic compounds such as hemoglobin have been used, e.g., in red blood cell vesicle reagents, and fluorogenic reporters have also been described, as indicated above. U.S. Pat. No. 3,887,698 to McConnell, et al discloses a liposome immunoassay test system in which the difference in electron paramagnetic resonance spectra between encapsulated and released nitroxide reporter provides a measure of complement-mediated liposome lysis. U.S. Pat. Nos. 4,235,792, to Hsia, et al. and 4,342,826, to Cole disclose liposome immunoassay systems in which complement-mediated cell lysis is evidenced by the expression of liposome-encapsulated enzymes.

Among the several types of reporter molecules whlch can be used, encapsulated enzymes offer a number of advantages over smaller chromogenic, fluorogenic or paramagnetic reporter molecules. Unlike smaller reporter molecules, enzymes show very little leakage on storage, or release due to nonspecific lysis in the presence of complement. Therefore, background levels in the immunoassay can be kept quite low. Many enzymes can participate in reactions which lead to detectable color changes, allowing an assay to be monitored visually, and, in any case, without the type of relatively expensive detecting apparatus which is required for determining released fluorogenic or paramagnetic reporters. Another important advantage of enzymes is the multiplication in sensitivity which is possible because of the high turnover of each enzyme molecule.

Despite the attractiveness of a lipid-vesicle immunoassay having encapsulated enzymes, difficulties in providing a satisfactory enzyme-encapsulated vesicle reagent have been encountered. Some enzymes, such as alkaline phosphatase, are present at relatively high levels in serum, and are therefore generally unsuitable for use in an assay system for determination of a serum analyte. Another major problem encountered is the difficulty in producing a vesicle reagent that has both (1) a high specific activity of an enoapsulated enzyme. and (2) a substantially oligolamellar lipid bilayer structure. Experiments conducted in support of the present invention, and reported below, indicate that complement-mediated vesicle lysis results in much higher levels of enzyme released from oligolamellar vesicles—defined as having one or a few lipid bilayer shells—than from multilamellar vesicles. The greater enzyme release, in turn, permits a considerably more sensitive homogeneous immunoassay.

A number of methods for producing large oligolamellar vesicles based on injecting a solution of lipid into an aqueous solution have been described (references 4–6). These methods give relatively poor encapsulation efficiencies, and therefore are impractical for use in producing a reagent having encapsulated enzyme with high specific activity. A reverse phase evaporation method for producing oligolamellar vesicles under conditions of relatively high encapsulation efficiency has been described (reference 7). Heretofore, however, inactivation of enzymes by exposure to the organic solvent or solvents and to sonication used in the method have limited the use of the method in forming vesicles having encapsulated enzymes.

Another limitation of encapsulated-enzyme liposomes which has been encountered is the difficulty in storing an enzyme-encapsulated liposome reagent without serious loss of enzyme activity over relatively short storage periods, such as a few weeks.

SUMMARY OF THE INVENTION

It is therefore a general object of the invention to provide an encapsulated-enzyme liposome immunoassay reagent, and method of forming same, which substantially overcome above-discussed problems associated with the prior art.

A more specific object of the invention is to provide such a reagent composed of oligolamellar vesicles encapsulating an enzyme at high specific activity.

A related object is to provide such a reagent which is stable on storage.

Still another object of the invention is to provide an immunoassay system and method employing such reagent for determination of serum analytes, and particularly serum analytes, such as theophylline, phenytoin, phenobarbital, digoxin, and serum peptides.

The reagent of the invention includes a suspension of oligolamellar lipid vesicles containing encapsulated glucose-6-phosphate dehydrogenase (G6PD). at a specific activity of between about 1–15 and preferably 5–15 units/μmole vesicle lipid, and glucose-6-phosphate (G6P) at a concentration of between about 2 and 50 mM, and preferably between about 5–25 mM. The vesicles have surface-bound. ligand molecules adapted to bind specifically and with high affinity to soluble anti-ligand molecules.

The reagent is formed by emulsifying a solution of G6PD, at a preferred concentration of at least about 50 units/ml, and G6P. at a concentration of at least about 2–5 mM, in an organic-solvent solution of vesicle-forming lipids, and subsequently removing the organic solvent to produce the vesicles. The surface ligand molecules may be included in the lipids used in forming the vesicles. or may be covalently attached to the vesicle surface lipids after vesicle formation.

The reagent is used in a method for determination of an analyte, which may be either a ligand or ligand-like analyte, in a competitive inhibition assay, or an anti-ligand type analyte, in a direct-binding assay. The reagent and analyte are mixed under conditions (e.g., in the presence of soluble anti-ligand in a competitive inhibition assay) which lead to ligand/anti-ligand binding on the vesicle surface in proportion to the amount of analyte present in the mixture. Complement-mediated, ligand-specific vesicle lysis resulting from the addition of serum complement leads to release of enzyme in proportion to the amount of reagent ligand/anti-ligand binding which has occurred. The amount of released enzyme is determined by the addition of a suitable substrate reporter system.

A system for practicing the method includes the reagent, anti-ligand antibody, in the case of a competitive inhibition assay. complement, and the substrate reporter system.

These and other objects and features of the present invention will become fully apparent when the following detailed description of the invention is read in conjunction with the accompanying drawings. The system shows good linearity and sensitivity in a competitive inhibition test for a variety of serum drug analytes, including theophylline, phenytoin, and phenobarbital.

BRIEF DESCRIPTION OF THE DRAWINGS

FIG. 1 shows steps in the synthesis of a phenytoin/lipid derivative used in one embodiment of the invention:

FIG. 2 shows steps in the synthesis of a phenobarbital/lipid derivative used in another embodiment of the invention;

DETAILED DESCRIPTION OF THE INVENTION

A. Preparing the Lipid-Vesicle Reagent

Figure 3:
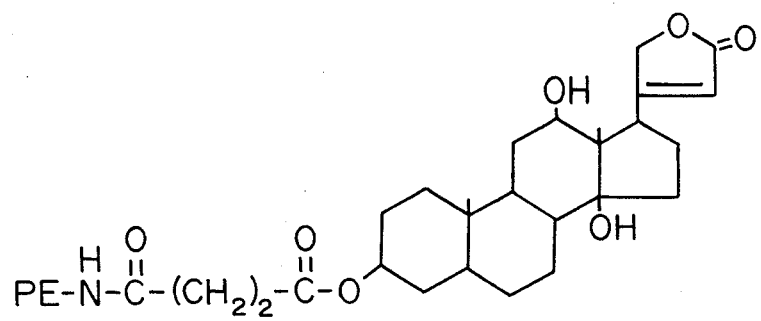
FIGS. 3 illustrates a dixogin/lipid derivative used in yet another embodiment of the invention.

The lipid-vesicle reagent of the invention is preferably formed by a reverse phase evaporation method in which a solution of the material to be encapsulated is first emulsified in an organic-phase solution of vesicle-forming lipids. After removing the organic solvent by evaporation, the resulting gel-like mixture is dispersed in an aqueous medium to form a suspension of vesicles encapsulating the originally emulsified material. The general principles underlying the reverse phase evaporation method are described in U.S. Pat. No. 4,235,871, and in reference 7. The method is particularly advantageous in forming relatively large, oligolamellar Vesicles under conditions of high encapsulation efficiency (up to about 50%).

The lipids used in forming the lipid vesicles, or liposomes, typically include lipid mixtures composed predominantly of phospholipid(s) and sterol(s). A list of phospholipids used commonly in liposome preparations is given on Page 471 of reference 8. The vesicles may be formulated to include negatively charged lipids, such as phosphatidic acid (PA), phosphatidylglycerol (PG), and phosphatidylserine (PS), to provide a desired surface charge on the reagent vesicles. In addition, the reagent is formulated to include either the molecules which will make up the surface ligand molecules in the final reagent, or one or more lipid components to which the ligands can be covalently attached, after vesicle formation. Examples of lipophilic and lipid-derivatized antigens which are suitable tor inclusion in the initial lipid formulation are discussed below, as are various methods for coupling ligand molecules, and typically macromolecular biomolecules. such as proteins, to preformed vesicles. The lipid mixture may further include stabilizers, and/or antioxidants, such as α-tocopherol, useful in extending the storage life of the reagent. A typical lipid mixture used in forming the reagent of the invention. such as the reagent described in Example I, includes between about 40-50% phosphatidylcholine (PC), 10% PG, 40% cholesterol, 5% ligand-derivatized lipid or lipid to which ligand molecules can be coupled, and about 0.1% α-tocopherol, all calculated on a mole percent basis. A trace amount of radiolabeled lipid, such as $^{125}$I-labeled PE, may be included for purposes of quantitating vesicle lipid.

The vesicle-forming lipids are dissolved in an inert organic solvent or solvent system, to form an oorganic-phase solution of the lipids. The types of organic solvents, and considerations in the selection of particular solvents or the solvent systems, are discussed in U.S. Pat. No. 4,235,871. As a general rule, the solvent or solvent system is one in which the lipid components can be readily dissolved, at the concentration in the range of between about 0.5-50 mg lipid/ml solvent, and which has a density which allows formation of relatively stable water-in-oil emulsions, i.e., a density similar to that of the aqueous phase used in forming the vesicles. Studies conducted in support of the present invention show that diethylether, either alone or in a solvent system composed of trichlorotrifluoroethane:ether (1:1) or chloroform:ether (1:3), are suitable solvents for practicing the invention.

The aqueous phase solution used in forming the reagent vesicles is a solution of G6PD and G6P, at selected concentrations, in a suitable buffer. The buffer is selected to produce minimal inactivation of the enzyme under the vesicle-preparation conditions employed. The buffer is preferably an isotonic salt solution, such as 0.15M NaCl, buffered to a PH of between about 5-7, and preferably about pH 6. phosphate and Tris buffers are suitable.

The enzyme solution is prepared to contain preferably about between 50-5000 enzyme units/ml aqueous phase, and more preferably between about 300-5000 units/ml, where a G6PD enzyme unit is defined as the amount of enzyme which can reduce 1 μmol of NAD per minute at room temperature in the presence of 300 mM Tris-HCl PH 7.8, 3.1 mM G6P. and 0.75 mM NAD. The study reported in Example I indicates that under optimal substrate-concentration conditions (discussed below), G6PD at an aqueous-phase concentration of about 300 units/ml can be encapsulated without appreciable loss of enzyme activity. At enzyme concentrations of about 3000 units/ml, 30-40% loss of activity occurs during vesicle formation. Even though enzyme inactivation is greater at higher enzyme concentrations, these higher concentrations are advantageous in forming vesicles having a relatively high specific activity of encapsulated enzyme. The preferred specific activity of encapsulated enzyme in the reagent of the invention is between about 1-15 and more preferably, 5-15 units/μmole vesicle lipid, and is achieved by employing an initial aqueous-phase enzyme solution whose enzyme concentration is between about 500-5000 units/ml. The G6pD may be derived from a commercially available bacterial source such as purified *Leuconostoc mesenteroides* G6PD.

According to an important feature of the invention, the agueous phase is prepared to include the enzyme substrate G6P to protect the enzyme against inactivation during the vesicle-preparation procedure. Experiments conducted in support of the application indicate that a G6P concentration as low as about 2 mM is effective in reducing enzyme inactivation during vesicle preparation. As will be seen in Example I below, in the G6P concentration range between 8 mM and 80 mM lower substrate concentrations are more effective in protecting the enzyme against inactivation during vesicle preparation, both at relatively low and relatively high enzyme concentrations. preferred substrate concentrations for practicing the invention are between about 5 and 50 mM, and preferably between 5 and 25 mM. The decreased protection against enzyme inactivation seen at high G6P concentrations may be due, at least in part, to contaminants in the G6P preparation which either block enzyme protection or accelerate enzyme inactivation. In such case, higher levels of contaminant-free G6p would be suitable in forming the reagent of the invention.

The aqueous-phase enzyme solution just described is added to the lipid solution at a volume ratio calculated to produce an emulsion of the water-in-oil type. preferably the ratio of aqueous phase and organic phase is between about 1:2 to 1:50 v/v. and most preferably about 1:3. The heterogeneous, two-phase mixture is emulsified, for example, by ultrasonic radiation, to produce a water-in-oil emulsion consisting of aqueous-phase emulsion particles suspended in the lipid solution. Typically, the temperature of the 2-phase mixture during the emulsification step is maintained at room temperature or below and emulsification is carried out by bath sonication for 1-5 minutes. The emulsion is then treated by evaporation, during which most or all of the lipid solvent is removed, to form a gel-like mixture of the lipids and aqueous-phase material. Evaporation is conveniently carried out by the use of a rotary evaporator at a temperature of about 20° C., under vacuum pressure of between about 20-50 mmHg. A small amount of water or buffer can be added to the gel mixture, and the resulting mixture evaporated for an additional period, for example about 15 minutes, to help remove residual traces of the lipid solvent.

Following removal of the organic solvent, thé gel mixture is converted to a suspension of lipid vesicles containing co-encapsulated G6PD and G6P, by dispersing the evaporated mixture in a suitable aqueous medium. An isotonic salt solution at pH between about 6-8, is suitable. The gel may be dispersed in the aqueous medium by gentle vortexing or the like. Under usual preparation conditions, the vesicles have average diameter sizes between about 2000-4000 Å and are composed predominantly of between one and a few bilayer shells. As used herein the term "oligolamellar" defines vesicles having one to a few lipid bilayer shells. The reagent has a preferred enzyme specific activity of between 1-10, and preferably 5-10 units/μmole vesicle lipid, as noted.

Following vesicle formation, the vesicles are separated from unencapsulated enzyme and substrate by centrifugation, molecular-sieve chromatography, or the like. In a typical procedure, the suspension is passed through a Sephadex G-200 or Bio-Gel A15m molecular sieve column, which gives rapid separation of the vesicles from unencapsulated material. The percent of total enzyme which is encapsulated in the oligolamellar vesicles, calculated as the ratio of encapsulated enzYme activity to total activity used in the vesicle preparation, is typically between about 10% and 20%. The nonencapsulated enzyme collected from the vesicle-separation step may be concentrated and reused in vesicle preparation.

Another vesicle-formation method which has been reported to produce relatively high encapsulation efficiency has been described (reference 9). This method involves first forming a suspension of small unilamellar vesicles (SUVs), mixing the vesicles with a solution of the solute to be encapsulated, and lyophilizing the vesicle/solute mixture under rapid freezing conditions. Upon slow rehydration, the SUVs apparently reform as larger vesicle structures, encapsulating a portion of the solute material during this vesicle reformation. Since the method does not involve direct exposure of the enzyme to be encapsulated to an organic solvent, as in the reverse evaporation method, it was of interest to determine whether the enzyme G6PD is also protected against inactivation by the presence of the enzyme substrate during vesicle preparation. Lipid vesicles were prepared, substantially as described in reference 9, using various enzyme concentrations ranging from about 160 to 740 enzyme units/ml, in an SUV/enzyme mixture, either in the presence or absence of 15 mM G6P. The total enzyme activity in the final vesicle preparation formed in the presence of substrate was about 83% of the initial total enzyme activity. whereas the enzyme was substantially totally inactivated in the absence of added substrate.

The addition of substrate to the enzyme during lipid vesicle preparation is thus seen to prevent enzyme inactivation by contact with lipids in a lyophilized lipid/enzyme mixture. as well as by exposure to organic solvents, in a water-in-oil emulsion containing the enzyme. The lyophilization method is generally less desirable. however, in forming a reagent for use in the immunoassay methods described in Section II. Experiments performed in support of the present invention indicate that a reagent formed by the lyophilization procedure gives much lower levels of released enzyme on ligand-specific complement-mediated lysis. Presumably this effect is due to the more multilamellar structure of the vesicles formed by the lyophilization procedure.

The reagent vesicles of the invention are also prepared to include a surface array of ligand molecules adapted to bind specifically and with high affinity to analyte-related anti-ligand molecules. As used herein, the term "ligand" refers broadly to either species in a binding pair composed of a target molecule having one or more specific epitopic features, and a target-binding molecule which recognizes such features, to bind the target molecule specifically and with high affinity. "Anti-ligand" refers to the other of the two species in the binding pair. Among the binding pairs which are contemplated by the present invention are antigen-antibody, immunoglobulin-protein A, carbohydrate-lectin biotin-avidin and hormone-hormone receptor protein. More generally, the ligand (or anti-ligand) may include any fragment or portion of the corresponding binding pair which is capable of participating with the opposite member of the pair in specific, high-affinity binding. For example, in an antibody-antigen pair, the binding ligand may include antigen-binding $F(ab')_2$ or $Fab'$ fragments.

In the reagent constructed specifically for use in a liposome immunoassay involving complement-mediated liposome lysis, the binding pairs have the property that the ligand/anti-ligand complex which forms on the vesicle surface is capable of activating either the classical or alternative complement pathway, initiating the complement reactions which lead to vesicle lysis. (The complement system is reviewed in references 10-12.)

A variety of methods are available for attaching ligand molecules to the surface of lipid vesicles. Where the ligand is a lipid antigen or an antigen-lipid conjugate. such may be included in the lipids forming the vesicles, as noted above, producing vesicles having outer surface arrays of the incorporated ligand molecules. Examples of lipid antigens which may be used as surface ligands in the invention include cardiolipin, glycosides, and gangliolipids.

Water-soluble antigens are preferably attached to the liposomes by covalent attachment to the polar end groups of lipid components of the liposomes. Experiments conducted in support of the present invention indicate that the antigen molecules must be spaced from the lipid component by a spacer arm for optimal assay sensitivity. The need for a spacer arm is presumably related to the greater ease of anti-antigen antibody binding to surface-bound antigen which is spaced somewhat from the liposome outer surface. Best assay results are achieved with a spacer arm length between about 2-10 atoms. With shorter chain lengths, antibody binding to the antigen appears to be sterically inhibited. Chain lengths greater than about 10 atoms may allow the acyl chain and/or antigen to bend and become buried in the liposome bilayer, also inhibiting antibody binding. A preferred type of spacer arm is an acyl chain of the form $(CH_2)_n$ where $n = 2-10$. Acyl chains have been found in experiments conducted herein to give greater assay sensitivity than chains containing internal polar groups, such as carboxyl or amide groups, which may interfere with antibody binding by hydrogen bonding effects. For example. it has been found that an acyl chain having an intermediate amide group is not functional in a complement-mediated liposome-lysis reaction where the ligand attached to the chain is either phenobarbital or phenytoin.

There are two general methods for coupling a water-soluble antigen to a lipid component through a spacer arm. In the first method, the spacer arm is first attached to a lipid component, and preferably to pE, through an amide linkage involving the lipid amine. Methods for attaching a dicarboxylic acid-type spacer arms to pE are detailed in co-owned U.S. patent applications for "Lipid Coupling Reagent and Method", U.S. patent application Ser. No. 692,679, filed 18 Jan. 1985, and "Liposome Composition and Method", application Ser. No. 766,776, filed 16 Aug. 1985, a continuation-in-part of the first mentioned application. In the '679 application, the spacer arm carries a terminal carboxyl group which is activated. for example by a soluble carbodiimide for amide coupling to a free amine group on the antigen. The '776 application describes a spacer arm having an aotive N-hydroxysuccinimide coupling group at the end of the spacer arm, for direct coupling to an amine group in the antigen.

Where the antigen does not contain a free amine group, a second general method of coupling may be used. Here the antigen is first reacted with an alkylating agent which includes a spacer arm and a terminal acid group. After alkylating the antigen, the acid group can be activated—for example, with a lipid-soluble carbodiimide—for attachment to a lipid amine, and preferably PE. This general approach is detailed in Example VII, for preparation of a PE-Phenytoin derivative; in Example IX, for preparation of a PE-phenobartital derivative; and in Example XI, for preparation of a PE-digoxin derivative.

Liposomes containing the antigen-coupled lipid components are easily prepared, as above, by including the lipid components in the lipids used in forming the vesicles. Alternatively, lipid antigens and lipid-antigen conjugates may be introduced into preformed vesicles by lipid exchange, as discussed in reference 13 and U.S. Pat. No. 4,483,929 for "Liposomes with Glycolipid-Linked Antibodies".

In forming a reagent whose surface ligands are large biomolecules, such as polypeptides or proteins, the ligand molecules typically are covalently attached to activated lipid components on the surface of preformed lipid vesicles. Several methods are available for coupling biomolecules covalently to the polar head groups of lipids. One method involves Schiff-base formation between a lipid aldehyde group and a primary amino group on the ligand molecule. The aldehyde group is formed by periodate oxidation, and the coupling reaction, after the removal of the oxidant, is carried out in the presence of a reducing agent. As reported in reference 14, the reaction can be used to couple up to 200-300 $\mu$g of protein, such as immunoglobulin G (IgG) per $\mu$mol of lipid vesicle lipid.

A second efficient coupling method known in the art is applicable to thiol-containing molecules, such as antibody fragments, and involves the formation of a disulfide or thioether bond between the vesicle lipid and ligand molecules attached. The method, which is described particularly in references 15 and 16, can produce a coupling of up to 600 $\mu$g of protein (IgG), per $\mu$mol of Vesicle lipid. After attachment of the ligand molecules, the vesicles are readily separated from free ligand, e.g., by centrifugation or molecular-sieve chromatography.

According to another important feature of the invention, the reagent may be stored at refrigerator temperature for periods of up to at least eight months without significant loss of enzyme activity or leakage of enzymes into the extraliposomal phase of the vesicle suspension. Experiments conducted in support of the invention show that the stability of the enzyme on storage is due to the presence of encapsulated G6P in the vesicle reagent. The effect of encapsulated substrate on the stability of the encapsulated enzyme in the reagent is seen in Example II below. In the absence of encapsulated substrate, vesicle-associated G6PD loses substantially all of its activity over a several-week storage period at refrigerator temperature. With added substrate, the enzyme shows substantially no loss of activity for up to at least eight months. The concentration of G6P in the vesicles is, of course, that used in vesicle preparation, i.e., between about 2-50 mM or higher, and preferably between about 5-25 mM.

B. Lioosome Immunoassay Methods

This section describes the use of the above vesicle reagent in two general types of homogeneous liposome immunoassays In the first immunoassay type, the analyte to be detected is a soluble anti-ligand species which binds directly to reagent ligand molecules, to form ligand/anti-ligand binding complexes on the vesicle surfaces. In the presence of added complement, ligand-specific, complement-mediated cell lysis releases encapsulated G6PD in proportion to the amount of analyte bound to the vesicles. The detectable enzyme activity is therefore directly proportional to the amount of analyte being determined. This assay type is also referred to as a direct-binding homogeneous assay.

The assay reaction is carried out in a reaction medium whose pH and ionic strength are compatible both with ligand/anti-ligand binding and with complement-mediated cell lysis. The osmolarity of the reaction medium is adjusted to produce the desired osmolarity gradient across the reagent vesicles, the reaction preferably being carried out at an osmolarity similar to that of the vesicle reagent.

The concentration of reagent vesicles in the assay medium is preferably adjusted such that the complement-mediated ligand-specific enzyme release from the vesicles continues to increase with the addition of increasing amounts of analyte, within the concentration range of analyte to be tested. Typical reagent vesicle concentrations are in the range between about $10^{-12}$ and $10^{-7}$ mol lipid per ml total assay volume. The complement is typically added to a final concentration of between about 2-100 $\mu$l of undiluted complement serum per ml assay volume. The complement may additionally be formulated to include small unilamellar vesicles (SUVs), prepared in accordance with co-owned patent application for "Blood-Fluid Composition System for Cell Lysis System", Ser. No. 583,095, filed 23 Feb. 1984. Studies conducted in support of the present invention showed minor improvement in test sensitivity, due to reduced background, by the addition of SUVs to the complement, either before or after complement addition to the assay reaction mixture. This effect is likely due to a suppression of serum interference with ligand-/anti-ligand binding. However, it is noted that another problem addressed in the above-cited patent application—to reduce nonspecific release of reporter molecules from liposomal target cells seen in the presence of complement—is much less serious with large enzyme-reporter molecules than with small fluorescent molecules examined in the earlier application.

In a typical immunoassay, the lipid vesicle reagent may be initially preincubated with serially diluted analyte samples, such as diluted serum samples. A control assay, used for measuring nonspecific enzyme release, is carried out in the absence of added anti-ligand analyte. Following preincubation—typically carried out for about 10 min at room temperature—a source of complement and optionally, SUVs, is added, and the assay mixture is incubated further, typically at room temperature for 30 minutes. The percent enzyme released is then determined by adding to the reaction mixture, a reporter system which allows detection of released enzyme. Alternatively, the assay can be carried out in a single step, combining the preincubation and complement-addition steps into a single incubation.

The level of G6PD released may be measured by monitoring the reduction of NAD to NADH at 340 nm. Although this method is simple and direct, it suffers from the limitations that NAD itself has a relatively low extinction coefficient and also that the reagent mixture may have a relatively high background level at 340 nm, due to the absorbance of interfering components present in the complement serum added to the assay.

The limitations noted above can be overcome in a reporter system containing, in addition to NAD, a dye which shows a relatively strong color change upon reduction by NADH in the presence of a suitable electron carrier. One dye which has been used successfully in the immunoassay of the invention is dichloroindophenol (DCIP) whose extinction coefficient is about three times that of NAD, at maximum absorption wavelengths, and which shows a readily detectable loss of blue color upon reduction by NADH in the presence of an electron carrier suc as phenazine methosulfate (PMS).

The total amount of released enzyme may be measured kinetically, by following the change in substrate or dye absorption over an initial time period. More conveniently, the reaction may be allowed to proceed substantially to completion, with the absorption of reduced substrate or dye being measured after stopping the reaction. In the latter case and where the reduced species being monitored is a dye, the reaction is stopped by the addition of a solvent which acts to prevent rapid reoxidation of the dye. In the reporter system composed of NAD, DCIP and PMS, it has been found that the addition of ethanol, to a final concentration to about 30% is effective in stopping the reaction and preventing reoxidation of the dye for a period of at least about 20 minutes at room temperature.

The direct-binding immunoassay just described is illustrated in Example IV below, which details a procedure for determination of anti-DNp antibody. At the analyte concentrations used, ligand-specific, complement-mediated lysis gave a detectable enzyme level of about 80% of the total encapsulated enzyme in the reagent. That the detectable enzyme level was accounted for largely by G6PD enzyme released from the vesicles (rather than by influx of substrate in cofactor in the lysed vesicles) is confirmed by the study in Example III, showing up to about 75% enzyme release under conditions of ligand-specific, complement-mediated lysis.

Examples VIII, X, and XII provide further examples of direct-binding immunoassays for determination of antibodies specific against liposome-bound ligands. The assay described in Example VIII, which involves a liposome reagent having surface-bound phenytoin (5,5-diphenylhydantoin), shows progressively greater enzyme release with greater amounts of anti-phenytoin antibody over a serial dilution range of 1:500 to 1. A similar assay in Example X involving liposomes with surface-bound phenobarbital (5-ethyl-5-phenyl barbituric acid) also shows progressively greater enzyme release with addition of greater amounts of anti-phenobarbital antibody over a serial dilution range of 1:500 to 1. In Example XII, a liposome reagent having surface-bound digoxin (digoxigenin) was used to assay for added anti-digoxin antibody. The amount of enzyme released was proportional to the amount of antibody added over a serial dilution range of 1:2, 500 to 1.

A second general type of immunoassays involves competitive inhibition between a ligand or ligand-like analyte and reagent vesicle ligand for binding to soluble anti-ligand also included in the immunoassay. The considerations relating to assay medium and concentrations of liposome reagent discussed above are generally applicable to this type of assay. The antibody is preferably added at a concentration which, in the absence of competing analyte molecules, leads to release of about 50% of the maximum releasable enzyme activity in the presence of complement. At this antibody concentration, the assay shows good linearity between analyte concentration and enzyme release over the broadest analyte concentration range.

According to one important finding herein, complement is preferably added to the assay mixture in a severalfold excess of that required to produce maximal liposome lysis in the presence of a given amount of antibody. Initial testing of a battery of serum samples, using the theophylline liposome reagent, showed that serum from patients who tested positive for either lupus erythrematous or syphilis also gave false positives for the presence of serum theophylline. That is, the serum gave reduced liposome lysis, as evidenced by reduced measurable enzyme, suggesting analyte inhibition. From follow-up studies it appears that serum from lupus(+) and syphilis(+) individuals inhibits one or more complement components, and this effect is seen as reduced liposome lysis. The complement inhibition effect was completely eliminated by increasing the amount of complement added to the assay mixture fourfold. For example, an original assay mixture containing 10 $\mu$l of complement gave maximum assay sensitivity with regard to analyte inhibition, but showed false positives with some lupus(+) and syphilis(+) serum. The same assay containing 40 $\mu$l of complement showed equivalent assay sensitivity but almost no false positives. (Two possible positives among 255 sera tested were observed, and these two sera also tested positive in a commercial theophylline test). The additional complement increased the extent of non-specific lysis observed (in the presence of complement but absence of anti-ligand antibody) 1 or 2% at most.

A competitive inhibition test may be performed by initially combining the reagent, the soluble anti-ligand antibody and the analyte, and incubating typically for about 10 min at room temperature. Following this, a source of complement is added, the reaction mixture is further incubated under conditions leading to complement lysis. The amount of enzyme released is measured as in the direct-binding assay. However, in the preferred assay, the liposome reagent, antibody, analyte, complement and enzyme substrate are combined together, and the assay is carried out in a single step which does not include preincubation.

Competitive inhibition assays of the type just described are illustrated in Examples V and VI (for theophylline), Example VIII (for phenytoin), and Example X (for phenobarbital). As seen from the examples, all of the assays are sensitive and give good linearity in the serum drug concentration ranges which are normally tested for in human serum.

The sensitivity and reliability of the assay system of the invention is due, in part, to the high specific activity of encapsulated G6PD in the assay reagent. As indicated above, enzyme-specific activities of between about 5-10 enzyme units per $\mu$mol of lipid are readily achievable. Another important factor in assay sensitivity and reliability is the oligolamellar nature of the reagent formed by the reverse evaporation method, which allows reporter enzyme molecules to be released from the reagent efficiently on complement-mediated reagent lysis. The study reported in Example III indicates that up to about 75% of the encapsulated enzyme is released from the vesicles on complement-mediated lysis. By contrast, reagent vesicles formed under conditions which lead to more multilamellar structures, such as by the lyophilization method described above, show relatively poor release (15-20%) of enzyme by complement-mediated lysis. The more multilamellar vesicles have been found, in studies conducted in support of the present invention, to give a detectable change in enzyme activity, as measured by the reduction of NAD by the enzyme at 340 nm, of about 0.1 OD over the test range of the system. By contrast, the assay procedure which employs the reverse-phase evaporation vesicles can be prepared to give a range of measurable enzyme activities over the test range between minimum and maximum analyte concentrations, of greater than 1.0 OD at 340 nm (Example VI).

From the foregoing, it can be appreciated how various objects and features of the invention are met. The reagent provides high sensitivity and reliability in a homogeneous immunoassay, due to the oligolamellar nature of the reagent vesicles, which permits efficient enzyme release on complement-mediated lysis, and to the high specific activity of the enzyme encapsulated in the reagent.

The reagent is readily prepared under conditions which lead to efficient enzyme encapsulation, and enzyme which is not encapsulated may be reused, since minimum enzyme inactivation occurs during the vesicle preparation step. The reagent, and particularly the total detectable enzyme activity thereof, is stable on storage for periods of up to at least eight months at refrigerator temperatures. Since serum and other blood-fluid samples do not themselves contain appreciable levels of NAD-requiring G6PD, the G6PD enzyme released in the immunoassay can be readily distinguished over background levels. (Mammalian G6PD has a requirement for an NADp cofactor, and cannot utilize the NAD present in the assay mixture.) Further, where the deteotion system includes a dye which can be reduced by NADH in the presence of a suitable electron carrier, to undergo a detectable color change, the problem of serum components at 340 nm can be avoided.

The following examples illustrate various aspects of the invention, but are in no way intended to limit the scope of the invention.

EXAMPLE I

Effect of Enzyme and Substrate Concentration on Enzyme Lability

Phosphatidylcholine (PC) and phosphatidylglycerol (PG) were obtained from Avanti Polar Lipids (Birmingham, AL); phosphatidylethanolamine derivatized with theophylline (T-PE) was prepared by a modification of the method of reference 17.

PC (2.2 μmol), PG 0.5 μmol), cholesterol (2.0 μmol), T-pE (0.25 μmol), α-tocopherol (0.005 μmol), and trace amounts of $^{125}$I-pE were dissolved in 1 ml of diethyl ether. Aqueous enzyme solutions containing either buffer, G6P, or NAD, at one of the concentrations indicated in the second column in Table I below, and G6PD at concentrations calculated to give the total enzyme units shown in the central column in Table I in 0.325 ml, were prepared in a suitable buffer with an osmolarity of about 350 mOs. Each of the reagent compositions shown in Table I was prepared by mixing 1 ml of the lipid solution with 0.325 ml of one of the twelve enzyme solutions. Each mixture was emulsified by sonication for 1 min, maintaining the temperature of the mixture at or below about room temperature. The ether solvent was removed under reduced pressure at room temperature, and the resulting dispersion was taken up in 0.3 ml of a preparation buffer.

Each of the reagent suspensions was assayed for total enzyme activity by incubating the suspension in an enzyme assay mix containing 300 mM Tris-HCl, pH 7.5, 4 mM G6P, 1 mM NAD, and 0.5% Triton X-100 for 20 min at room temperature. The reaction was terminated by raising the pH to 10 with 1M Na$_2$CO$_3$. The amount of NAD reduced was measured at 340 nm. One unit of enzyme is defined as the amount of enzyme which can reduce 1 μmol of NAD per min at room temperature in the above buffer. The enzyme activity values measured are shown in the fourth column in Table I, and expressed as percent of original enzyme activity in the last column.

TABLE I

| Sample No. | Substrate/ Cofactor | G6PD added (units) | G6PD recovered units | G6PD recovered % |
|---|---|---|---|---|
| 1 | — | 85 | 7 | 8 |
| 2 | — | 57 | 15 | 26 |
| 3 | 8 mM G6P | 31 | 29 | 94 |
| 4 | 8 mM G6P | 96 | 100 | 104 |
| 5 | 8 mM G6P | 306 | 249 | 81 |
| 6 | 8 mM G6P | 1609 | 1029 | 64 |
| 7 | 15 mM G6P | 1127 | 694 | 62 |
| 8 | 25 mM G6P | 1127 | 494 | 44 |
| 9 | 80 mM G6P | 778 | 133 | 17 |
| 10 | 25 mM G6P | 17 | 16 | 94 |
| 11 | 8 mM NAD | 136 | 25 | 18 |
| 12 | 20 mM NAD | 118 | 0.1 | 0.1 |

In the absence of added substrate (first two less than about 25% of the original enzyme activity was recovered. Inactivation was largely prevented, at enzyme concentrations of less than about 100 units (per 0.325 ml) by the addition of 8 mM substrate. At enzyme concentrations above about 700 units/0.325 ml (Samples 6–9), optimal protection was provided at 8 mm G6P concentration and increasingly less protection, at substrate oonoentrations up to 80 mM. The data show that the enzyme cofactor NAD contributes to rather than protects the enzyme against inactivation.

EXAMPLE II

Stability of the Lipid Vesicle Reagent

Lipid-vesicle reagents having surface-bound theophylline were prepared as in Example I, using an initial enzyme solution containing up to 1000 units of G6PD in 0.325 ml and 8 mM of G6P. The lipid vesicles in the final suspension were separated from nonencapsulated material by molecular-sieve chromatography on Sephadex G-200 in a buffer containing 50 mM Tris-HCl, pH 7.5, and 250 mM glucose. The vesicle preparations were stored in Tris-HCl buffer, at 4° C., for increasing storage periods up to 4 months. An aliquot of the reagent was removed and assayed in the presence of Triton X-100, according to the procedure of Example I at a storage period indicated in Table II. The total observed activity is expressed in Table II in terms of percent of the initial activity.

TABLE II

| Preparation No. | Storage period (days) | Activity remaining (%) |
|---|---|---|
| 1 | 18 | 85 |
| 2 | 24 | 90 |
| 3 | 24 | 82 |
| 4 | 39 | 103 |
| 5 | 75 | 100 |
| 6 | 93 | 26 |
| 7 | 105 | 51 |
| 8 | 120 | 118 |

As seen from the data, encapsulated G6PD is were obtained for preparations 6 and 7. By contrast, reagent vesicles prepared in the absence of added substrate showed low initial activity, due to enzyme inactivation during preparation, and almost complete loss of activity on storage at refrigerator temperature over a few-week period.

EXAMPLE III

Complement-Mediated Enzyme Release

This example demonstrates that G6PD enzyme activity detected on ligand-specific, complement-mediated lysis is due predominantly to release of encapsulated enzyme from lysed vesicles, rather than to infusion of additional substrate and/or cofactor into the lysed vesicles.

A purified vesicle reagent composed of a suspension of vesicles encapsulating G6PD and substrate. and having surface-bound theophylline ligand molecules, were prepared as in Example II, using an enzyme solution containing 31 units of G6PD per 0.325 ml and 8 mM substrate. Anti-theophylline-BSA rabbit serum was obtained from Western Chemical Research (Fort Collins, Colo.). Guinea pig serum was obtained from Miles Scientific (Naperville, Ill.).

The purified lipid vesicles (0.18 μmol) were incubated first with anti-theophylline antibody (40 μl), then with complement (420 μl) in 0.66 ml of the above assay buffer, for 60 min at room temperature. The reaction was stopped by adding EDTA to a final concentration of 6 mM. The lysed vesicles were immediately chromatographed on Sephadex G-200, in the same assay buffer, to separate vesicles from released enzyme. A control reaction mixture in which buffer was substituted for complement was incubated under identical conditions. For both the control and complement(+) assay mixtures, the G6PD activity of (1) the total mix applied to the column, (2) the material retained at the top of the column, (3) that in the free enzyme fraction. and (4) lipid vesicle material in the void volume were separately determined, according to the assay method described in Example I. Also for each of these four fractions, the total amount of lipid was determined from the level of $^{125}I$ radioactivity of $^{125}I$-PE added to the liposome as a tracer. The enzyme and $^{125}I$ levels in the four fractions for both the control and complement(+) samples are shown in Table III below.

TABLE III

|  | G6PD activity (units) control complement (+) | | $^{125}I$ (CPM) control complement (+) | |
|---|---|---|---|---|
| applied to col. | 0.102 | 0.100 | 4282 | 3655 |
| at top of col. | 0.074 | 0.004 | 3295 | 1023 |
| free enz. frac. | 0.006 | 0.075 | 176 | 782 |
| REV fraction | 0.004 | 0.006 | 64 | 822 |

The data in the table indicate that in the control assay sample most of the vesicle lipid and enzyme activity is retained at the top of the column. possibly reflecting vesicle aggregation which has occurred during the assay reaction. Only about 6% of the enzyme is present in the control free enzyme fraction, indicating very little enzyme release. This result contrasts with that obtained in the complement(+) assay, in which about 75% of the enzyme is in the free enzyme fraction. Given the relatively small amount of lipid measured in the free enzyme fraction, it is apparent that a major portion of the encapsulated enzyme has been released by complement-mediated lysis.

EXAMPLE IV

Direct Binding Immunoassay

N-dinitrophenylaminocaproyl pE (DNP-PE) was obtained from Avanti polar Lipids (Birmingham, Ala.). Goat antibody against DNp conjugated to bovine serum albumin (DNp-BSA) was obtained from Miles Lab (Elkhart, Ind.). and was reconstituted to about 1.4–1.8 mg antibody per ml.

A lipid vesicle reagent encapsulating G6PD and the substrate G6P, and carrying surface-bound DNP, was prepared substantially as in Example I, where 0.5 μmol of DNP-PE pwas substituted for 0.25 μmole T-PE used in Example I. The initial enzyme solution used in preparing the vesicles contained about 300 units G6PD/ml and 8 mM G6P. The vesicle suspension was purified by chromotography on a Sephadex G-200, as in Example II, to remove unencapsulated enzyme material. The vesicles were suspended in a Tris-HCl buffer, pH 7.5, to a final concentration of about 200 nmols/ml.

To demonstrate the use of the lipid reagent in a direct-binding immunoassay for determination of anti-DNp antibody, six fractions, each containing 100 μl of the lipid-vesicle reagent diluted 1:10 with Tris-HCl buffer, were prepared. To these samples were added 5 μl of antibody (Samples 3 and 6), 10 μl of 10% Triton X-100 (Sample 2), or 10 μl of dilution buffer (Samples 1, 4 and 5), as indicated in Table IV below. Following incubation for ten min at room temperature. 10 μl of dilution buffer (Samples 1–3) or 10 μl of complement (Samples 4–6) were added to the fractions, which were then incubated an additional thirty min at room temperature. At the end of the second incubation period, 1 ml of a substrate buffer containing the 30 mM of Tris-HCl, pH 7.5, 0.5 mM $MgCl_2$, 0.15 mM $CaCl_2$, 0.2M NaCl, 1 mM G6P, and 0.6 mM NAD, was added to each sample tube and the reaction mixture was incubated for twenty min at 37° C. The reaction in each tube was stopped by the addition of 1M $Na_2CO_3$ to a final concentration of 0.15M, and the OD of the samples was read at 340 nm. The results are shown in Table IV below. The enzyme activity in Sample 6, when corrected for antibody and complement background at 340 nm (Samples 3 and 4) and for nonencapsulated enzyme activity (Sample 1) gave the enzyme activity value shown in parentheses. The corrected 0.121 OD value obtained for ligand-specific, complement-mediated enzyme activity represented about 80% of the total vesicle enzyme level.

TABLE I

| Sample # | Vesicles | Sample | Complement | OD 340 nm |
|---|---|---|---|---|
| 1 | + | — | — | 0.008 |
| 2 | + | detergent | — | 0.150 |
| 3 | — | anti-DNP | — | 0.006 |
| 4 | — | — | + | 0.040 |
| 5 | + | — | + | 0.049 |
| 6 | + | + | + | 0.175 (0.121) |

EXAMPLE V

Competitive Inhibition Immunoassay

A lipid vesicle reagent encapsulating G6PD and G6P and carrying surface-bound theophylline ligand molecules was prepared as in Example I, using an enzyme solution containing about 1000 enzyme units/0.325 ml and a substrate concentration of 8 mM. The vesicles were purified from nonencapsulated material on Sephadex G-200 as in Example II. Rabbit anti-theophylline serum was ohtained from Western Chemical Research (Ft. Collins, CO) and diluted 1:100 with assay buffer. Theophylline was obtained from Sigma Chemical Co. St. Louis, Mo.).

To demonstrate the sensitivity and linearity of a competitive inhibition test using the lipid vesicle reagent of the invention, 0.01 ml of the reagent (about 1 μmole) was added to each of 12 sample tubes, and combined with either 30 μl of assay buffer (Samples 1, 2) or 30 μl of the diluted antibody, and to each sample was added 50 μl of buffer containing the various amounts of theophylline indicated in Table V below. After an initial incubation period of 10 min at room temperature, either 10 μl of buffer (Samples 1, 12) or 10 μl of guinea pig serum complement was added to a final volume of 100 μl, at 300 mM Tris-HCl, pH 7.5. 0.5 mM $MgCl_2$, and 0.15 mM $CaCl_2$, and incubated for an additional 30 min at room temperature.

Immediately following the second incubation step, 400 μl of buffer containing 250 mM Tris-HCl, pH 7.5, 1.25 mM NAD, and 5 mM G6P was added to each of the samples, and the assay mixture was incubated at 37° C. for 20 min. The reaction was stopped with 200 μl of 1.0M $Na_2CO_3$, and the optical density of the solution was read at 340 nm. The results obtained are shown in the fourth column in Table V.

Considering the data, the first three rows show various control enzyme values for nonencapsulated enzyme activity (row 1), nonencapsulated activity plus activity released nonspecifically by complement (row 2), and total activity measured in the presence of both complement and ligand-specific row 3. The row 3 value is taken as the zero inhibition value, as indicated at the right hand column in the table. This value compares with the total enzyme activity value of 1.1 measured in Sample 12 by the addition of Triton X-100 to the assay mixture. Comparing the two values, it is seen that about 85% of the total enzyme activity is expressed under conditions of specific, complement-mediated reagent lysis.

TABLE V

| Sample | Thoephylline (μg/ml) | Antibody | Complement | OD 340 nm | % Inhibit. |
|---|---|---|---|---|---|
| 1 | — | — | — | 0.062 | |
| 2 | — | — | + | 0.239 | |
| 3 | — | + | + | 0.958 | 0 |
| 4 | 4.06 | + | + | 0.399 | 78 |
| 5 | 0.406 | + | + | 0.577 | 56 |
| 6 | 0.081 | + | + | 0.664 | 41 |
| 7 | 0.041 | + | + | 0.728 | 32 |
| 8 | 0.020 | + | + | 0.769 | 27 |
| 9 | 0.010 | + | + | 0.796 | 23 |
| 10 | 0.005 | + | + | 0.887 | 10 |
| 11 | 0.0025 | + | + | 0.859 | 14 |
| 12 | — | (Triton X-100) | — | 1.100 | |

The OD values, when calculated on a semi-log scale as a function of theophylline concentration, are linear over the analyte range from about 0.01 to 4 μg/ml.

EXAMPLE VI

Competitive Inhibition Assay

A lipid vesicle reagent encapsulating G6PD and G6P and carrying surface-bound theophylline ligand molecules was prepared as in Example I, to a final encapsulated enzyme concentration of 11.6 units of enzyme/μmol of vesicle lipid and 8 mM encapsulated substrate. The buffer used in preparing the vesicles contained 40 mM sodium phosphate, pH 6.0, and 150 mM NaCl. The vesicles were purified from nonencapsulated material as in Example II. Commercial theophylline alibration standards (2.5, 5, 10, 20 and 40 μg/ml) and calibration controls were obtained from Bio Diagnostic, International (La Havra, CA). The calibration standards and calibration controls were each diluted 1:50 with an assay buffer containing 300 mM Tris-HCl. pH 7.8, 0.5 mM $MgCl_2$ and 0.15 mM $CaCl_2$. The 1:50 dilution was selected, based on the results from Example V, to produce assay linearity in the analyte range between about 2.5–40 μg/ml theophylline in serum. Rabbit anti-theophylline antibody was obtained from Western Chemical Research.

To each of 8 sample tubes was added 100 μl of one of the diluted theophylline calibration or control standards indicated in Table VI. Each theophylline sample was combined with 200 μl assay buffer containing 0.1 μl antibody, 10 l guinea pig complement and 15 μl 0.05M NAD, and 200 μl assay buffer containing 0.4 nmole liposome reagent and 30 μl of 0.1M G6P. The 500 μl assay mixtures were incubated at 37° C. for 30 min, and the reaction stopped with the addition of 150 μl 1M $Na_2CO_3$. The absorbance was read at 340 nm.

Figure 4:
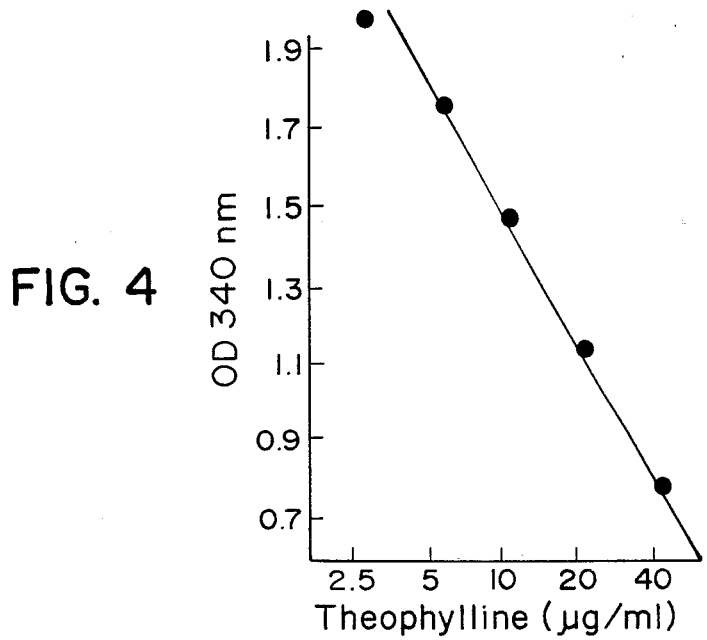
FIGS. 4–6 are plots showing enzyme release versus assay concentration of theophylline (FIG. 4). phenytoin (FIG. 5), and phenobarbital (FIG. 6).

The OD values from samples 1–5 were plotted on a semi-log scale as a function of μg/ml in the original calibration standards (FIG. 4). The data gives a substantially linear relationship between log theophylline concentration and OD reading. The standard curve obtained was used to determine the concentration of theophylline in high, intermediate, and low-theophylline concentration controls (samples 6–8) from the corresponding OD readings obtained for those samples. The control values determined from the standard curve are shown in the fourth column in Table VI, expressed in μg/ml. As seen from the data, each of the calculated values is well within the range of theophylline concentrations supplied by the manufacturer for each of the three different controls (and indicated at the right in Table VI).

TABLE VI

| Sample No. | [T] (μg/ml) | $OD_{340}$ | Controls (μg/ml) | Control Range (μg/ml) |
|---|---|---|---|---|
| 1 | 40 | 0.791 | | |
| 2 | 20 | 1.162 | | |
| 3 | 10 | 1.487 | | |
| 4 | 5 | 1.769 | | |
| 5 | 2.5 | 1.984 | | |
| 6 | high | 1.023 | 26.0 | 25.7–40.8 |
| 7 | in term. | 1.256 | 15.5 | 12.5–21.3 |
| 8 | low | 1.610 | 6.9 | 5.3–10.6 |

EXAMPLE VII

Preparation of DPPE-Phenytoin 5,5-diphenylhydantoin (phenytoin) was obtained from Sigma Chemical Co. (St. Louis, Mo.), and the methyl ester of 5-bromovaleric acid, from Aldrich Chemical Co. (Milwaukee, Wis.).

The dipalmitoylphosphatidyl ethanolamine (DPPE) amide of 3-(4-carboxybutyl(5,5-diphenylhydantoin (DPPE-phenytoin) was prepared as outlined in FIG. 1. Briefly, the sodium salt of 5,5-diphenylhydantoin (compound A) was formed by treatment with sodium hydroxide. The compound (10 mmoles) was reacted with the methyl ester of 5-bromovaleric acid (10.5 mmoles) in dimethyl formamide, substantially as described in referenc 18, to form the methyl ester of 3-(4-carboxybutyl)5,5-diphenylhydantoin (compound B). Following acid hydrolysis, the acid of 3-(4-carboxybutyl)5,5-diphenylhydantoin (220 μmoles) was reacted with a saturated solution of DPPE in chloroform in the presence of diclohexylcarbodiimide (DCCI) (220 μmoles)

and a molar excess of triethylamine (TEA) (440 μmoles). The reaction was carried out in a 12 ml reaction volume, with stirring for 72 hr at 23° C. The DPPE-phenytoin product (compound C) was purified by column chromatography, with a silica gel column, using a chloroform-methanol solvent system.

EXAMPLE VIII

Competitive Inhibition Assay for Phenytoin

Rabbit anti-phenytoin antibody was obtained from Western Chemical Res. Co. (Ft. Collins, Colo.) and was diluted 1:100 with assay buffer (Example III). phenytoin standard sera were obtained from Bio Diagnostic International (LaHabra, CA) and diluted to 1:50 in the assay buffer.

Liposomes containing encapsulated G6PD and surface-bound phenytoin were prepared substantially as described in Example I, using an enzyme solution containing about 1116 enzyme units/0.325 ml and a substrate concentration of 8 mM. DppE-phenytoin (Example VII) was included in the vesicle-forming lipids at a concentration of about 4.9 mole percent. After liposome preparation, free enzyme was removed by molecular-sieve chromatography. The liposomes had an encapsulated payload of about 7 units/μmole of lipid.

Initially a lysis experiment showing the response of the liposome reagent to increasing amounts of added antibody in the presence of complement was performed. The lipid vesicles (about 1 nmoles in 40 μl) were incubated with serial dilutions of anti-phenytoin antibody (25 μl). and 40 μl of complement (undiluted guinea pig serum) in a total volume of 500 μl. The reaction conditions and method of assaying released enzyme activity were substantially as described in Example 1. The results, given in Table VII below, show increasing liposome lysis with increasing antibody added, over the entire antibody dilution range tested. Complete lysis of liposomes was achieved with 25 μl of undiluted antibody.

TABLE VII

| Antibody Dilution | O.D. (340 nm) | Lysis (%) |
| --- | --- | --- |
| 1/500 | 1.890 | 44 |
| 1/250 | 2.200 | 53 |
| 1/125 | 2.580 | 63 |
| 1/62 | 2.700 | 66 |
| 1/31 | 2.952 | 72 |
| 1/16 | 3.000 | 74 |
| 1/8 | 3.060 | 75 |
| 1/4 | 3.222 | 79 |
| 1/2 | 3.536 | 88 |
| 1 | 4.000 | 100 |
| Detergent Lysis* | 4.006 | 100 |

Figure 5:
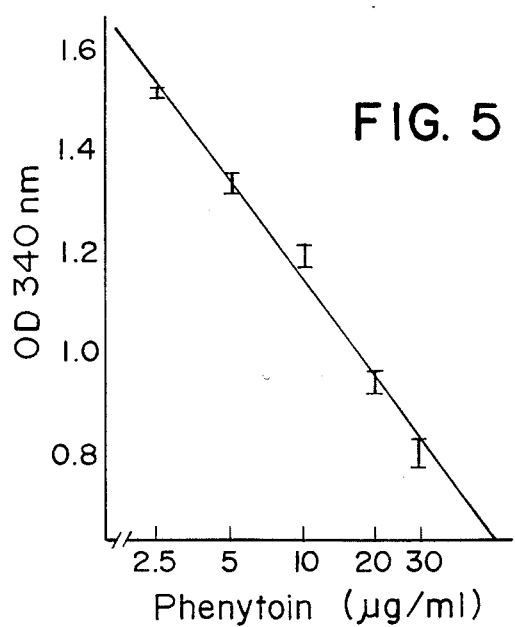

To demonstrate the sensitivity and linearity of a competitive inhibition test, 40 μl (about 1 nmole) of the DPPE-phenytoin liposome reagent was added to each of several tubes and combined with 10 μl of anti-phenytoin antibody, diluted 1:100 with assay buffer. The final antibody concentration is identical to that of the 1:250 dilution in the antibody-response test above, and produces about 50% maximum inhibition in the absence of added phenytoin. To each sample was added increasing amounts of phenytoin, as indicated in FIG. 5, to a final concentration of between 2.5 and 30 μg/ml—the range normally of interest in phenytoin blood testing. The assay mixture was incubated with 40 μl of guinea pig serum, NAD and G6P for 30 min at 37°.

The reaction was stopped with $Na_2CO_3$ and released G6PDH was assayed as above.

The results of the test are shown in FIG. 5, where the error bars indicate the range of duplicate assays. The figure shows good assay linearity and sensitivity in the phenytoin concentration range tested.

EXAMPLE IX

Preparation of DPPE-Phenobarbital 5-ethyl-5-phenyl barbituric acid (phenobarbital) was supplied from Cooper Biomedical Inc. (Mavern, pA), and the methyl ester of 5-bromovaleric acid, from Aldrich Chemical (Milwaukee, WI).

The DppE amide of 1-(4-carboxybutyl)-5-ethyl-5-phenyl barbituric acid (DPPE-phenobarbital) was prepared as outlined in FIG. 2. The sodium salt of phenobarbital (compound A) (2 mmoles) formed by treating phenobarbital with sodium hydroxide was reacted with the methyl ester of 5-bromovaleric acid (2.200 mmoles) in 5 ml of N,N-dimethyl formamide, for 4 hrs at 96° C., to form the methyl ester of 1-(4-carboxybutyl)-5-ethyl-5-phenyl barbiturate (compound B). The product was purified by column chromatography at a yield of about 77%.

Acid hydrolysis in aqueous dioxane was carried out for 2 hrs at 95° C., and the acid product was purified chromatographically. The resultant 1-(4-carboxybutyl)-5-ethyl-5-phenyl barbituric acid (220 μmoles) was reacted with a supersaturated solution of DppE (200 μmoles) in chloroform (12 ml) in the presence of diclohexylcarbodiimide (DCCI) (220 μmoles) and a molar excess of triethylamine (440 μmoles). The reaction was carried out in 12 ml with stirring for 48 hrs at 23° C. The DPPE-phenobarbital product (compound C) was purified by column chromatography, with a silica gel column, using a chloroform-methanol solvent system.

EXAMPLE X

Competitive Inhibition Assay for Phenobarbital

Rabbit anti-phenobarbital antibody was obtained from (Western Chemical Res. Co., Ft. Collins, Colo.). phenobarbital standards were diluted 1:50 in the assay buffer.

Liposomes containing encapsulated G6PD and surface-bound phenobarbital were prepared substantially as described in Example VII, with DPPE-phenobarbital being included in the vesicle-forming lipids at a concentration of about 4.9 mole percent. After liposome preparation, free enzyme was removed by molecular-sieve chromatography. The liposomes had an encapsulated payload of about 7 units/μmole of lipid.

As in Example VII, a lysis experiment showing the response of the liposome reagent to increasing amounts of added antibody in the presence of complement was performed. The lipid vesicles (about 1 nmole) were incubated with anti-phenobarbital antibody (25 μl) diluted with assay buffer as indicated in Table VIII, and with 40 μl of guinea pig complement in a total volume of 500 μl. The reaction was carried out, and the amount of enzyme released was determined as described above. The results show increasing liposome lysis with increasing antibody added and up to 94% lysis was achieved.

TABLE VIII

| Antibody Dilution | O.D.(340 nm) | Lysis (%) |
| --- | --- | --- |
| 1/500 | 0.110 | 4 |

TABLE VIII-continued

| Antibody Dilution | O.D.(340 nm) | Lysis (%) |
| --- | --- | --- |
| 1/250 | 0.236 | 8 |
| 1/125 | 0.954 | 33 |
| 1/62 | 1.867 | 64 |
| 1/31 | 2.13 | 73 |
| 1/16 | 2.24 | 76 |
| 1/8 | 2.31 | 79 |
| 1/4 | 2.48 | 85 |
| 1/2 | 2.69 | 92 |
| 1 | 2.76 | 94 |
| Detergent Lysis* | 3.17 | 100 |

Figure 6:
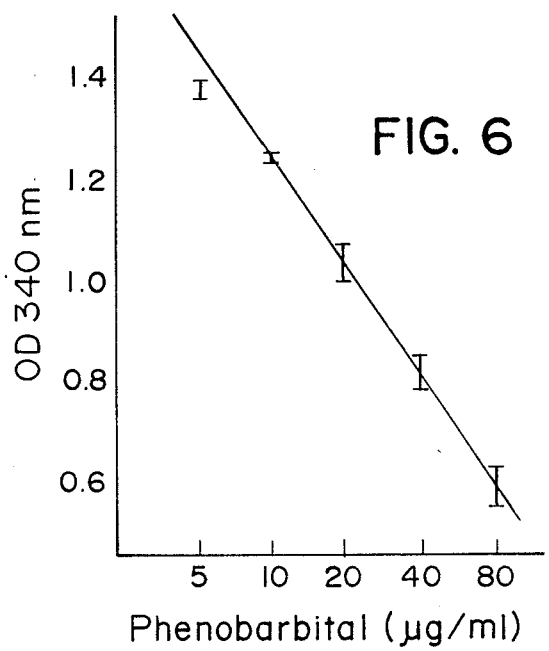

To demonstrate the sensitivity and linearity of a competitive inhibition test. 40 μl (about 1 nmole) of the DPPE-phenobarbital liposomes was added to each of several tubes and combined with 30 μl of anti-phenobarbital antibody, diluted 1:100 with assay buffer. To each sample was added increasing amounts of phenobarbital, as indicated in FIG. 6, to a final concentration of between 5 and 80 μg/ml, the range normally of interest in phenytoin blood testing. The mixture was incubated with complement, G6P and NAD for 30 min at 37° as described in Example VII. Released G6PDH was assayed as above.

The results of the test, seen in FIG. 6, show good assay linearity in the phenobarbital range of usual interest, similar to what was found in the theophylline and phenytoin assays.

EXAMPLE XI

Preparation of DPPE-Digoxigenin

Both digoxin and digoxigenin (the aglycon of digoxin) were obtained from Sigma Chemical (St. Louis, Mo.) and succinic anhydride from Aldrich Chemical (Milwaukee, Wis.).

This section describes the preparation of the PE amide of digoxigenin-3-hemisuccinate. As a first step, digoxigenin-12-acetate was prepared by reacting digoxigenin (250 μmoles) with acetic anhydride in 1 ml of pyridine. The partial acetylation reaction was carried out for 120 hrs at 23° C., and the product purified by column chromatograph, using a silica gel column and a methylene chloride-methanol solvent system. The yield was about 64%.

The digoxigenin-12 acetate was converted to digoxigenin-12-acetate-3-hemisuccinate by the method detailed in U.S. Pat. No. 3,855,208. Briefly, the acetate 157 μmoles) was mixed with succinic anhydride (700 μmole) in about 1 ml of pyridine. for 16 hrs at 75° C. Selective alkaline hydrolysis, by addition of potassium carbonate for 30 hrs at 23° C. yielded the digoxigenin-3-hemisuccinate. This product (210 μmoles) was reacted with a supersaturated solution of egg DPPE (200 μmoles) in 6 ml chloroform in the presence of diclohexylcarbodiimide (DCCI) (220 μmoles) and a molar excess of triethylamine (420 μmoles). The reaction was carried out with stirring for 72 hrs at 23° C. The DPPE-digoxigenin product was purified by column chromatography, with a silica gel column, using a chloroform-methanol solvent system. The structure of the compound is shown in FIG. 3.

EXAMPLE XII

Evaluation of Liposomes with DPPE-Digoxigenin

Rabbit anti-digoxigenin antibody was obtained from Western Chemical Res. Co. (Ft. Collins. Colo.).

Liposomes containing encapsulated G6PD and surface-bound digoxigenin were prepared substantially as described in Example I, using an enzyme solution containing about 578 enzyme units/0.325 ml and a substrate concentration of 8 mM. pE-digoxigenin-3-hemisuccinate from Example XI was included in the vesicle-forming lipids at a concentration of about 4.9 mole percent. After liposome preparation free enzyme was removed by molecular-sieve chromatography. The liposomes had an encapsulated payload of about 7.4 units/μmole of lipid.

The response of the liposomes to increasing quantities of added anti-digoxin antibody was assessed as in above Examples VIII and X. The lipid vesicles (about 1 nmole) were incubated with anti-digoxin antibody (25 μl) diluted with assay buffer as indicated in Table IX, and with 40 μl of complement. The reaction was carried out, and the amount of enzyme released was determined, as described in Examples VIII and X. As seen from the table, the antibody-complement-mediated lysis of digoxin-liposomes followed a pattern similar to that seen with theophylline, phenytoin, and phenobarbital.

TABLE IX

| Antibody Dilution | O.D. (340 nm) | Lysis (%) |
| --- | --- | --- |
| 1/2500 | 0.336 | 12 |
| 1/1250 | 0.874 | 30 |
| 1/625 | 1.464 | 51 |
| 1/250 | 1.901 | 66 |
| 1/125 | 1.905 | 66 |
| 1/62 | 1.953 | 68 |
| 1/25 | 1.939 | 67 |
| 1 | 2.66 | 92 |
| Detergent Lysis* | 2.89 | 100 |

While the invention has been described with reference to particular embodiments and examples, it will be appreciated that various changes and modifications can be made without departing from the spirit of the invention. In particular, although the reagent has been described for use in a homogeneous complement lysis assay, the reagent could be used advantageously in a solid-phase lipid vesicle immunoassay involving binding of the liposome reagent to a solid support, or in a homogeneous assay in which lipid vesicle lysis is produced by another type of ligand-specific lytic mechanism. For example, co-owned patent application for "Viral Lysis Assay", Ser. No. 612,421, filed 21 May 1984, describes a homogeneous lipid vesicle lysis assay involving ligand-specific viral-mediated lysis. It will be readily appreciated that, for any type of homogeneous or two-phase assay system, a wide variety of different ligand-/anti-ligand pairs can be substituted for the pairs described herein to illustrate the invention.

It is claimed:

1. A homogeneous enzyme immunoassay system for determination of a serum analyte, comprising
    anti-analyte antibody,
    an assay reagent composed of a suspension of oligolamellar vesicles encapsulating glucose-6-phosphate dehydrogenase at a specific activity of between about 1–15 units/μmole vesicle lipid, and glucose-6-phosphate, at a concentration of between about 5–50 mM, and carried on each vesicle, a surface array of ligand molecules adapted to compete with the analyte for binding to the anti-analyte antibody,
    complement adapted to react with the vesicles to effect vesicle lysis and release of encapsulated glucose-6-phosphate dehydrogenase, in proportion to the amount of anti-analyte antibody bound to the vesicle surfaces, and present in an amount which is severalfold in excess of the minimum amount needed to obtain a maximum degree of complement-mediated vesicle lysis in the presence of a given amount of anti-analyte antibody, and a reporter system adapted to react with released glucose-6-phosphate dehydrogenase, to produce a detectable spectral change, in proportion to the amount of enzyme released.

2. A method for determination of a serum analyte comprising, providing an assay reagent composed of a suspension of oligolamellar vesicles encapsulating glucose-6-phosphate dehydrogenase at a specific activity of at least about 1 unit/μmole vesicle lipid, and glucose-6-phosphate, at a concentration of between abut 5–50 mM, and having surface-bound ligand molecules adapted to bind anti-analyte antibody, mixing the reagent with an anti-analyte antibody and a serum sample to produce immunospecific binding of anti-analyte antibody to the vesicles in inverse proportion to the amount of analyte present in the serum sample, adding complement to the reagent to produce vesicle lysis in proportion to the extent of extent of immunospecific anti-analyte antibody binding to the vesicles, thereby releasing encapsulated glucose-6-phosphate dehydrogenase, wherein the complement is added in an amount which is severalfold in excess of the minimum amount needed to obtain a maximum degree of complement-mediated vesicle lysis in the presence of a given amount of anti-analyte antibody, and determining the amount of enzyme released from the vesicles.

3. A method for determination of a serum analyte comprising, providing an assay reagent composed of a suspension of oligomellar vesicles encapsulating glucose-6-phosphate dehydrogenase, at a specific activity of at least about 1 unit/μmole vesicle lipid, and having surface-bound ligand molecules adapted to bind anti-ligand analyte molecules, mixing the reagent with an analyte-containing serum sample to produce immunospecific binding of the analyte to the vesicles in proportion to the amount of analyte present in the serum sample, adding complement to the reagent to produce vesicle lysis in proportion to the extent of immunospecific analyte binding to the vesicles, thereby releasing encapsulated glucose-6-phosphate dehydrogenase, and determining the amount of enzyme released from the vesicles.

4. A homogeneous enzyme immunoassay system for determination of serum phenobarbitol, at a concentration of between about 5 to 80 μg/ml serum, comprising anti-phenobarbitol antibody, an assay reagent composed of a suspension of oligolamellar vesicles encapsulating glucose-6-phosphate dehydrogenase at a specific activity of between about 1–15 units/μmole vesicle lipid, and glucose-6-phosphate, at a concentration of between about 5–50 mM, and carried on each vesicle, a surface array of phenobarbitol molecules adapted to competer with serum phenobarbitol for binding to the anti-phenobarbitol antibody, complement adapted to react with the vesicles to effect vesicle lysis and release of encapsulated glucose-6-phosphate dehydrogenase, in proportion to the amount of anti-phenobarbitol antibody bound to the vesicle surfaces, and a reporter system adapted to react with released glucose-6-phosphate dehydrogenase, to produce a detectable spectral change, in proportion to the amount of enzyme released.

5. A homogeneous enzyme immunoassay system for determination of serum phenytoin, at a concentration of between about 2.5 and 40 μg/ml serum, comprising anti-phenytoin antibody, an assay reagent composed of a suspension of oligolamellar vesicles encapsulating glucose-6-phosphate dehydrogenase at a specific activity of between about 1–15 units/umole vesicle lipid, and glucose-6-phosphate, at a concentration of between about 5–50 mM, and carried on each vesicle, a surface array of phenytoin molecules adapted to compete with serum phenytoin for binding to the anti-phenytoin antibody, complement adapted to react with the vesicles to effect vesicle lysis and release of encapsulated glucose-6-phosphate dehydrogenase, in proportion to the amount of anti-phenytoin antibody bound to the vesicle surfaces, and a reporter system adapted to react with released glucose-6-phosphate dehydrogenase, to produce a detectable spectral change, in proportion to the amount of enzyme released.

6. A homogeneous enzyme immunoassay system for determination of serum digoxigenin, comprising anti-digoxigenin antibody, an assay reagent composed of a suspension of oligolamellar vesicles encapsulating glucose-6-phosphate dehydrogenase at a specific activity of between about 1–15 units/umole vesicle lipid, and glucose-6-phosphate, at a concentration of between about 5–50 mM, and carried on each vesicle, a surface array of digoxigenin molecules adapted to compete with serum digoxigenin for binding to the antidigoxigenin antibody, complement adapted to react with the vesicles to effect vesicle lysis and release of encapsulated glucose-6-phosphate dehydrogenase, in proportion to the amount of anti-digoxigenin antibody bound to the vesicle surfaces, and a reporter system adapted to react with released glucose-6-phosphate dehydrogenase, to produce a detectable spectral change, in proportion to the amount of enzyme released.

* * * * *